(12) United States Patent
Dumoutier et al.

(10) Patent No.: US 6,274,710 B1
(45) Date of Patent: Aug. 14, 2001

(54) ANTIBODIES WHICH SPECIFICALLY BIND T CELL INDUCIBLE FACTORS (TIFS)

(75) Inventors: Laure Dumoutier; Jamila Louhed; Jean-Christophe Renauld, all of Brussels (BE)

(73) Assignee: Ludwig Institute for Cancer Research, NY (US)

( * ) Notice: Subject to any disclaimer, the term of this patent is extended or adjusted under 35 U.S.C. 154(b) by 0 days.

(21) Appl. No.: 09/178,973

(22) Filed: Oct. 26, 1998

(51) Int. Cl.[7] ............................. C12P 21/08; C07K 16/24
(52) U.S. Cl. .................................. 530/387.9; 530/387.1; 530/387.3; 530/388.1; 530/388.23; 530/389.2
(58) Field of Search ........................... 530/388.2, 387.9, 530/387.1, 387.3, 388.1, 388.23, 389.2

(56) References Cited

FOREIGN PATENT DOCUMENTS

99/61617 * 12/1999 (WO) .
00/65027 * 11/2000 (WO) .

OTHER PUBLICATIONS

Parrish–Novak, et al., "Interleukin–21 and its receptor are involved in NK cell expansion and regulation of lymphocyte function," , Nature 408:57–63 (Nov. 2, 2000).*
Xie, et al., "Interleukin (IL–22), a Novel Human Cytokine That Signals Through the Interleukin Receptor–related proteins CRF 2–4 and IL–22R." J. Biol. Chem. 275 (40):51335–51339 (Oct. 6, 2000).*
Abaza et al. Journal of Protein Chemistry, 11(5):433–444, 1992.*

* cited by examiner

Primary Examiner—David Saunders
Assistant Examiner—Amy DeCloux
(74) Attorney, Agent, or Firm—Fulbright & Jaworski, LLP

(57) ABSTRACT

The invention involves isolation of nucleic acid molecules, the expression of which are upregulated by interleukin-9. The amino acid sequences of the proteins which correspond to the nucleic acid molecules show some structural features of cytokines. In addition to the nucleic acid molecules and the proteins, various uses of the molecules are disclosed. The molecules are referred to as T cell induceable factors.

8 Claims, 1 Drawing Sheet

FIG. 1

Sequence homology between human and mouse TIF

```
SEQ ID NO:27 mTIF    MAVLQKSMSFSLMGTLAASCLLLIAIWAQEANALPVNTRC              40
SEQ ID NO:28 hTIF    ****   **  ****** ****    **   **
                     MAALQKSVSSFLMGTLATSCLLLIALLVQGAAAPISSHC mTIF    KLEVSNFQQPYITVNRTFMLAKEASLADNNTDVRLIGEKLF             80
                     ** * ***** ***********************
             hTIF    RLDKSNFQQPYITNRTFMLAKEASLADNNTDVRLIGEKLF mTIF    RGVSAKDQCYLMKQVLNFTLEDVLLPQSDRFQPYMQEVVP              120
                      *  ************ * *****************
             hTIF    HGVSMSERCYLMKQVLNFTLEEVLFPQSDRFQPYMQEVVP mTIF    FLTKLSNQLSSCHISGDDQNIQKNVRRLKETVKKLGESGE              160
                      ** * * *    ***********
             hTIF    FLARLSNRLSTCHIEGDDLHIQRNVQKLKCTVKKLGESGE mTIF    IKAIGELDLLFMSLRNACV                                   179
                     ******************
             hTIF    IKAIGELDLLFMSLRNACI                                   179
```

ANTIBODIES WHICH SPECIFICALLY BIND T CELL INDUCIBLE FACTORS (TIFS)

FIELD OF THE INVENTION

This invention relates to newly isolated nucleic acid molecules and their uses. The nucleic acid molecules are shown to be upregulated by the cytokine interleukin-9 ("IL-9"). Also disclosed are the proteins encoded thereby. They are described as T Cell Derived Inducible Factors ("TIFs"). These nucleic acid molecules encode proteins which induce STAT activation in cells.

BACKGROUND AND PRIOR ART

The last decade has seen knowledge of the immune system and its regulation expand tremendously. One area of particular interest has been that of research on the proteins and glycoproteins which regulate the immune system. One of the best known family of these molecules, are the cytokines. These are molecules which are involved in the "communication" of cells with each other. The individual members of the cytokine family have been found to be involved in a wide variety of pathological conditions, such as cancer and allergies. Whereas sometimes the cytokines are involved in the pathology of the condition, they are also known as being therapeutically useful.

Interleukins are one type of cytokine. The literature on interleukins is vast. An exemplary, but by no means exhaustive listing of the patents in this area includes U.S. Pat. Nos. 4,778,879 to Mertelsmann et al.; 4,490,289 to Stern; 4,518,584 to Mark et al.; and 4,851,512 to Miyaji et al, all of which involve interleukin-2 or "IL-2". Additional patents have issued which relate to interleukin-1 ("IL-1"), such as U.S. Pat. No. 4,808,611 to Cosman. The disclosure of all of these patents are incorporated by reference herein. More recent patents on different interleukins include U.S. Pat. Nos. 5,694,234 (IL-13); 5,650,492 (IL-12); 5,700,664, 5371,193 and 5,215,895 (IL- 11); 5,728,377, 5,710,251, 5,328,989 (IL-10); 5,580,753, 5,587,302, 5,157,112, 5,208,218 (IL-9); 5,194,375, 5 4,965,195 (IL-7); 5,723,120, 5,178,856 (IL-6), and 5,017,691 (IL-4). Even a cursory review of this patent literature shows the diversity of the properties of the members of the interleukin family. One can assume that the larger cytokine family shows even more diversity. See, e.g., Aggarwal et al., ed., Human Cytokines: Handbook For Basic And Clinical Research (Blackwell Scientific Publications, 1992), Paul, ed., Fundamental Immunology (Raven, Press, 1993), pg 763–836, "T-Cell Derived Cytokines And Their Receptors", and "Proinflammatory Cytokines and Immunity". All cited references are incorporated by reference.

The relationships between various cytokines are complex. As will be seen from the references cited herein, as the level of a particular cytokine increases or decreases, this can affect the levels of other molecules produced by a subject, either directly or indirectly. Among the affected molecules are other cytokines.

The lymphokine IL-9, previously referred to as "P40", is a T-cell derived molecule which was originally identified as a factor which sustained permanent antigen independent growth of T4 cell lines. See, e.g., Uyttenhove et al., Proc. Natl. Acad. Sci. 85: 6934 (1988), and Van Snick et al., J. Exp. Med. 169: 363 (1989), the disclosures of which are incorporated by reference, as is that of Simpson et al., Eur. J. Biochem. 183: 715 (1989).

The activity of IL-9 was at first observed on restricted T4 cell lines, failing to show activity on CTLs or freshly isolated T cells. See, e.g., Uyttenhove et al, supra, and Schmitt et al., Eur. J. Immunol. 19: 2167 (1989). This range of activity was expanded when experiments showed that IL-9 and the molecule referred to as T cell growth Factor III ("TCGF III") are identical to MEA (Mast Cell Growth Enhancing Activity), a factor which potentiates the proliferative response of bone marrow derived mast cells to IL-3, as is described by Hültner et al., Eur. J. Immunol. and in U.S. patent application Ser. No. 498,182 filed Mar. 23, 1990 the disclosures of both being incorporated by reference herein. It was also found that the human form of IL-9 stimulates proliferation of megakaryoblastic leukemia. See Yang et al., Blood 74: 1880 (1989). Recent work on IL-9 has shown that it also supports erythroid colony formation (Donahue et al., Blood 75(12): 2271–2275 (Jun. 15, 1990)); promotes the proliferation of myeloid erythroid burst formation (Williams et al, Blood 76: 306–311 (Sep. 1, 1990); and supports clonal maturation of BFU-E's of adult and fetal origin (Holbrook et al., Blood 77(10): 2129–2134 (May 15, 1991)). Expression of IL-9 has also been implicated in Hodgkins's disease and large cell anaplastic lymphoma (Merz et al., Blood 78(8): 1311–1317 (Sep. 1, 1990). Genetic analyses of mice that were susceptible or resistant to the development of bronchial hyperresponsiveness have unraveled a linkage with the IL-9 gene as well as a correlation between IL-9 production and susceptibility in this model (Nicolaides et al., Proc. Natl. Acad. Sci. USA, 94, 13175–13180, 1997). Human genetic studies also point to the IL-9 and IL-9R genes as candidates for asthma (Doull et al., Am. J. Respir. Crit. Care Med., 153, 1280–1284, 1996; Holroyd et al., Genomics 52, 233–235, 1998). Secondly, IL-9 transgenic mice allowed for the demonstration that increased IL-9 expression result in lung mastocytosis, hypereosinophilia, bronchial hyperresponsiveness and high levels of IgE (Temann et al., J. Exp. Med. 188, 1307–1320, 1998; Godfraind et al., J. Immunol. 160, 3989–3996, 1998; McLane et al., Am. J. Resp. Cell. Mol. In press). Taken together, these observations strongly suggest that IL-9 plays a major role in this disease.

IL-9 is known to affect the levels of other molecules in subjects. See Louahed et al. J. Immunol. 154: 5061–5070 (1995; Demoulin, et al., Mol. Cell. Biol. 16: 4710–4716 (1996), both incorporated by reference. It will be recognized that the molecules affected have their own functions in biological systems. For example, Demoulin et al. show that many of the known activities of IL-9 are mediated by activation of STAT transcription factors. As such, there is continued interest in trying to identify molecules whose presence and/or level is affected by other molecules, such as cytokines.

The disclosure which follows describes such molecules. It was found that nucleic acid molecules encoding the proteins of the invention were expressed in the presence of IL-9, but not in its absence. Hence, these molecules are, inter alia, "markers" for the expression or effect of IL-9 in a subject. The molecules are referred to as T Cell Derived Induced Factors or "TIFs" hereafter. These, and other features of the invention will be seen in the disclosure which follows.

BRIEF DESCRIPTION OF THE FIGURES

FIG. 1, presents sequence information.

DETAILED DESCRIPTION OF PREFERRED EMBODIMENTS

Example 1

The murine lymphoma cell line BW5147 is well known as a cell line which can be grown in vitro, without the need to add any cytokines to its culture medium. In order to identify genes induced by IL-9, samples of BW5147 were cultured either with (200 U/ml), or without IL-9, for 24 hours. Then, total RNA was isolated, using guanidium isothiocyanate lysis, and CsCl gradient centrifugation. These techniques are well known in the art. Following this, polyadenylated RNA was purified from the total RNA, by using an oligo(dT) cellulose column. The isolated, polyA RNA was then used to generate double stranded cDNA. A commercially available oligo(dT) primer was used. Anywhere from 3–5 ug of polyA RNA were heated to 70° C. for 10 minutes with 1 µg of oligo dT, and then incubated with 5× first strand buffer (250 mM HCl (pH 8.3), 375 mM KCl, 15 mM $MgCl_2$), 10 mM dithiothreitol, 500 uM of deoxynucleotide triphosphates, and 800 U of reverse transcriptase. Total volume of the reaction mixture was 20 ul, and the reaction was allowed to proceed at 37° C. for one hour. This resulted in synthesis of the first stand of cDNA. Second strand synthesis was accomplished by adding 30 ul of 5 second strand buffer (100 mM Tris-HCl(pH 6.9)), 450 mM KCl, 23 mM $MgCl_2$, 0.75 mM β-$NAD^+$, 50 mM $(NH_4)_2SO_4$ together with 60 U of E. coli derived DNA polymerase I, 2 U of E. coli RNase H, 10 U of E. coli DNA ligase, and 250 uM of deoxynucleotide triphosphates, and brought to a final volume of 150 ul. The mixture was incubated for two hours, at 16° C.

The product was extracted using phenol-chloroform, and was precipitated with ethanol. The final cDNA product was then resuspended in 200 µl of TE.

These steps were carried out for both the stimulated BW5147 cells ("tester" hereafter), and for parallel, unstimulated BW5147 cells ("driver" hereafter).

Example 2

The cDNA prepared in Example 1 was then subjected to subtraction cloning in accordance with well known methods. To do this, six oligonucleotides were prepared:
5'-AGCACTCTCC AGCCTCTCAC CGCA-3 (SEQ ID NO: 1);
5'-GATCTGCGGT GA-3'(SEQ ID NO: 2);
5'-ACCGACGTCG ACTATCCATG AACA-3'(SEQ ID NO: 3);
5'-GATCTGTTCA TG-3'(SEQ ID NO: 4);
5'-AGGCAACTGT GCTATCCGAG GGA-3'(SEQ ID NO: 5); and
5'-GATCTTCCCT CG-3'(SEQ ID NO: 6).
These were used as explained herein. Double stranded cDNA (2 ug), was digested with restriction endonuclease DpnII, extracted with phenol-chloroform, precipitated with ethanol, and resuspended in 20 ul of TE (10 MM Tris-HCl (pH 7.5); 1 mM EDTA). Twelve ul (1.2 ug), of cut cDNA was ligated to double stranded SEQ ID NOS: 1 and 2, in a mixture which included 4 ul of desalted SEQ ID NO: 1 (2mg/ml), 4 ul desalted SEQ ID NO: 2 (1 mg/ml), 10 µl of 5× adapter buffer (330 mM Tris-HCl, pH 7.6, 50 mM $MgCl_2$, 5 mM ATP), 7 µl DTT (100 mM), and 28 µl of $H_2O$). The oligonucleotides were annealed to each other and to the sample DNA, by heating the mixture to 50° C., and then cooling it to 10° C. over one hour, followed by adding 5 ul of T4 DNA ligase, and incubation for 12–14 hours, at 12–16° C. The mixtures were diluted by adding 140 ul of TE. PCR was then carried out on 200 ul samples, as described infra.

Example 3

To carry out PCR, 200 ul samples containing 2 ul of the ligation product in a buffer of 66 mM Tris-HCl, pH 8.8, 4 MM $MgCl_2$, 16 mM $(NH_4)_2SO_4$, 33 ug/ml BSA, 0.3 mM of each dNTP (concentration: 500 µM), and 2 ug of SEQ ID NO: 2 were first heated at 72° C. for three minutes, to remove any of SEQ ID NO: 1 which was hybridized to the product of Example 2. The 3' ends were then filled in, by using 5 U of Taq polymerase (5 minutes, 72° C.). Twenty cycles of amplification were carried out (1 cycle: 1 minute at 95° C., and three minutes at 72° C.), after which products were combined, phenol extracted, ethanol precipitated, and resuspended in TE buffer, at a concentration of 0.5 ug/ul. Hereinafter, this is referred to as the representation.

Example 4

The representation was then prepared for subtractive hybridization by removing SEQ ID NO: 1 therefrom by digestion with Dpn II. The resulting digest was phenol extracted and ethanol precipitated. In the case of the unstimulated sample, this resulted in the driver, while the stimulated sample resulted in the tester. Portions of tester (20 ug), were gel purified, on a 1.2% agarose gel, and isolated. Samples (2 ug), were ligated to SEQ ID NOS: 3 and 4, in the same way that SEQ ID NOS: 1 and 2 were ligated, as described, supra.

In a first cycle of subtractive hybridization, 0.4 ug samples of tester with SEQ ID NOS: 3 and 4 ligated thereto were mixed with 40 ug of driver cDNA. The mixture was phenol extracted, ethanol precipitated, dissolved in 2 ul of 3XEE buffer (30 mM EPPS pH 8.0), 3 mM EDTA); pH 8.0, 3 mM EDTA. This was overlaid with 30 ul of mineral oil, and denatured for five minutes at 98° C. A 5 M NaCl solution (0.5 ul), was added, and DNA was hybridized for 20 hours, at 67° C. The reaction mixture was diluted to 200 ul with TE, and tRNA carrier. The samples were incubated for three minutes at 72° C. to melt away SEQ ID NO: 4, and then four PCR reactions (200 ul), were prepared. These included 20 ul of diluted hybridization mix without primer, to fill in the ends of the reannealed tester, followed by 10 cycles of amplification after adding samples of SEQ ID NO: 3 (1 cycle: 1 minute at 95° C., three minutes at 70° C.) after which products were combined, phenol extracted, ethanol precipitated, and resuspended in 40 /µl of 0.2×TE buffer. Single stranded DNA was degraded by a 30 minute treatment of 20 µl of this material with 20 U of mung bean nuclease, at a total volume of 40 ul. Samples was diluted (1:5), in 50 mM Tris-HCl, at pH 8.9, followed by five minutes of heating at 98° C., to inactivate the enzyme. A second PCR was carried out, using 20 ul of the product described supra, 2 ul of SEQ ID NO: 3 (1 mg/ml), and 1 ul (5 U) of Taq DNA polymerase. A total of 18 cycles (1 cycle:1 minute at 95° C., three minutes at 70° C.), were carried out. Products were combined, phenol extracted, ethanol precipitated, and resuspended at 0.5–1 ug/µl. The product is referred to hereafter as "DP1", or the first difference product.

Example 5

DP1 was then digested with endonuclease DpnII, as described above, and was ligated to SEQ ID NOS: 5 and 6, following the same processes described for SEQ ID NOS: 1, 2, 3 and 4. Subtractive hybridization and selective amplification, as described in example 4 was repeated, and second difference product, or "DP2", was generated. In these experiments, 50 ng of DP1 was the tester. The driver (40 ug), was as described supra. The process was repeated to generate a third difference product, using SEQ ID NOS: 3 and 4 as adapters. To generate the third product, 100 pg of tester were mixed with 40 µg of driver. All steps of the protocols supra were repeated, except the final amplification was carried out for 22 cycles, where one cycle was one minute at 95° C., and three minutes at 70° C. This yielded the final difference product.

Example 6

The final difference products were digested with DpnII, and then cloned into the BamHI site of a commercially available vector, i.e., ptZ19R. Double stranded DNA plasmids were prepared, and then sequenced, using standard methods. The sequences were compared to known sequences in the GenBank and EMBL data bases, using a BLAST search program.

At the end of this subtraction procedure, a short cDNA fragment was identified, i.e., a fragment about 200 base pairs long. This fragment was used to screen a cDNA library from BW 5147 cells. The largest clone was sequenced. It is discussed infra. It does not correspond to any known sequence.

The nucelotide sequence is 1121 bases long, including a 537 base pair open reading frame, which encodes a protein 179 amino acids long. The predicted molecular weight of the protein is 20,093.

Analysis of the sequence shows three, AT rich motifs (TTATTTAT). These motifs are often found in 5'-untranslated regions of cytokines and oncongenes. Kruys, et al., Science 245: 852 (1989), have shown that these repeats modulate stability of mRNA for TNF.

FIG. 1 presents, inter alia SEQ ID NO: 7, with the AT regions referred to supra being boxed, and the polyadenylation sequence (AATAAA) underlined.

Example 7

The cDNA isolated and analyzed in example 6, supra, was then used as a probe to identify genomic DNA for TIFα.

A genomic library was prepared from mouse strain 129, and screened with SEQ ID NO: 7, following standard methods. An EcoRI fragment from a positive clone was subcloned, into plasmid pZERO, and partially sequenced. The partial sequence is presented as SEQ ID NO: 8.

Example 8

A second EcoRI fragment from the positive clone described in Example 7, supra, was also subcloned. There was a great deal of homology, but the sequences were not identical. To be specific, intron 1 of this sequence was 98% identical to SEQ ID NO: 8, intron 2 was 100% identical and intron 3 was 92% identical.

What is striking about the sequences is that the promoters are not at all homologous, suggesting independent regulation. The 5' untranslated regions are 92% identical. The first exon for TIFα is split into exon 1α and exon 1β. The first coding exon (which is exon 1b for TIFα and exon 1 for TIFβ) are 99.5% identical, while the second exons are 100% identical, the third exons 97% identical, the fourth exons 98.5% identical, and 96% for the fifth exon. In the untranslated 3'-region, homology is 96%.

Example 9

Using the information described in example 8, supra, a cDNA sequence for the second clone designated TIFβ was deduced, and is set forth as SEQ ID NO: 9.

As compared to the coding region for TIFα, that of TIFβ has six silent changes. There are two changes which result in an inconsequential amino acid change (at both of positions 36 and 113, Val in TIFα becomes Ile in TIFβ). There is also a more significant change, at position 112, where Gln becomes Arg.

Example 10

Experiments were undertaken to study expression of the TIFs. BW 5147 cells were stimulated with recombinant murine IL-9 (200U/ml), for varying periods of time (0.2, 0.5, 1, 2 & 24 hours). Total RNA was then isolated, using standard methods and reagents. Reverse transcription was then carried out, using 5, μg total RNA and an oligo (dT) primer. Samples of cDNA corresponding to 20 ng of total RNA were then amplified for 25 cycles using different primers. (One cycle was 4 minutes at 94° C., 1 minute at 57° C, and 2 minutes at 72° C). The TIF primers were:
5'-CTGCCTGCTT CTCATTGCCC T-3' (SEQ ID NO: 10) and
5-CAAGTCTACC TCTGGTCTCA T-3' (SEQ ID NO: 11) (sense and antisense, respectively).

These correspond to nucleotides 106–126, and 764–784 of SEQ ID NO: 7, respectively. As a control, β-actin was amplified as well, for 18 cycles (first cycle: 4 minutes at 94° C., 1 minute at 60° C., 2 minutes at 72° C. Succeeding cycles were 1 minute at 94° C, 1 minute at 60° C., 2 minutes at 72° C.).

Following amplification, post PCR products were analyzed on a 1% agarose gel, and specific amplification was confirmed, following blotting, using internal radioactive probes. The probe for TIF was:
5'-GACGCAAGCA TTTCTCAGAG-'3' (SEQ ID NO: 12)
the conditions and probes set forth were not specific for one or the other of the forms of TIF; however, the amplification product of TIFα contains a KpnI restriction site, while the restriction site for TIFβ does not. Digestion of the amplification products with KpnI indicated that most, if not all of the TIF mRNA induced by IL-9 was TIFα.

Example 11

Experiments were then carried out which showed that the induction of TIF MRNA by IL-9, described supra, does not require protein synthesis. In these experiments, total RNA was extracted from cells stimulated for 24 hours, as described in example 10, but with or without 10 μg/ml of a protein synthesis inhibitor, cycloheximide for 4.5 hours. In a parallel set of experiments, cells were not stimulated. The total RNA was extracted, and RT-PCR amplification was carried out as described in example 10. Post-PCR products were analyzed on an ethidium bromide-stained, 1% agarose gel. What was seen was that the induction by IL-9 still occurred when protein synthesis was blocked. Hence, the effect of IL-9 is a direct effect , not requiring the synthesis of a protein mediator.

Example 12

In these experiments, the role of STAT proteins in induction of TIF mRNA was studied on derivatives of the cell line BW5147. The first line, BWh9R expresses wild type human IL-9 receptors. The line BW-Phel 116 is a transfectant with a single mutation (at position 116), which renders the receptor unable to activate STAT transcription factors. Still another cell line, BW-mut6 has a mutation which renders the receptor unable to activate STAT5, while retaining the ability to activate STAT1 and STAT3. Finally, cell line BW-mut7 has a single mutation which renders the IL-9 receptor unable to activate STAT1, and STAT3, but which retains the ability to activate STAT5.

Cell stimulation, isolation of total RNA, reverse transcription and amplification of cDNA were all carried out as described in example 10 (Cells were stimulated for 24 hours. Both human and murine recombinant IL-9 were used). The PCR products were analyzed on an ethidium bromide stained, 1% agarose gel, as describe supra.

The analysis revealed that human IL-9 did not induce expression in BW-Phe116, suggesting that STAT transcription factors are implicated. It was found that IL-9 induced TIF expression in the BW-mut6 mutant, but not the mut7 variant, suggesting that STAT1 or STAT3 are involved, but not STAT5.

Example 13

The expression of TIF mRNA in normal mouse spleen cells was then studied.

Spleen cells from 10–12 week old, Balb/c mice were cultured for 24 hours in control medium or the control medium supplemented with 20 µg/ml of LPS (which activates B lymphocytes and macrophages), or ConA (which activates T cells), or ConA plus 1% of a blocking antiserum against murine IL-9, with β actin being used as a control. Purification of RNA, RT-PCR analysis were carried out as described 5 supra.

The data indicated that TIF is, at best, very weakly expressed in resting spleen cells, not induced by LPS, but strongly induced by ConA. Anti IL-9 antiserum did not affect induction by ConA, suggesting that its effect is not mediated by IL-9, or is mediated by other cytokines.

When the ConA activated spleen cells were analyzed using sequences of RT-PCR products, it was found that these cells were expressing TIFα predominantly, or exclusively. This is in contrast to the BW5147 cells, which expressed TIFα.

Example 14

Further experiments showed that TIF mRNA was expressed even in the absence of IL-9 induction.

Spleen cells from 5 week old, FVB mice, were enriched for T cells, using a nylon wool column. Then, the cells were stimulated for 24 hours in medium supplemented with ConA (a T cell activator), or PMA (which activates PKC in most cells), either with or without IL-9.

Total RNA was isolated using standard techniques, and then ten microgram samples were fractionated via electrophoresis on a 1.3% agarose gel containing 2.2 M formaldehyde. The fractions were then transferred to a nitrocellulose membrane, labeled, and assayed in a hybridization assay following Van Snick. et al., J. Exp. Med. 169: 363 (1989), incorporated by reference.

The results indicated that the induction of TIF by ConA was not modified, i.e., IL-9 did not induce TIF RNA.

Example 15

The expression of TIF mRNA in various cell lines was tested. In these experiments, murine cell lines were stimulated for at least one day, with a particular cytokine. Specifically, 9T7 is a T cell lymphoma, which responds to IL-2, IL-4 or IL-9. Cell lines TS3 and TS6 are derived from T helper cell clones, and proliferate in the presence of either IL-2 or IL-9. MC9 and LI38 are mast cell lines, which proliferate in the presence of either. IL-3 or IL-9.

Following stimulation, total RNA was prepared using standard guanidium isothiocyanate lyses, and CsCl gradient centrifugation.

The 9T7 line was then analyzed by Northern blotting, as described in example 14, while the other lines were assayed using RT-PCR analysis, as described supra.

It was found that IL-9 upregulated TIF expression in T helper cells, and mast cells, while IL-2 and IL-3 did not. The 9T7 cell line, however, showed roughly the same level of expression, regardless of the cytokine, indicating that IL-9 is not mandatory for TIF expression.

Example 16

The expression of TIF mRNA in B cell lines was then studied. The cell lines A20, 70Z/3, and BCL-1 are B cell leukemia cell lines which grow, in vitro, without cytokines. These cells were stimulated for 24 hours with IL-4 and Il–9 and total RNA was isolated, using standard methods. Expression was analyzed by RT-PCR which was carried out for 35 cycles, followed by blotting and hybridization, as described supra.

The results indicated that TIF expression is detectable in B cells, but is weakly upregulated at best in the presence of IL-9 and IL-4.

Example 17

Experiments were then carried out to study expression of the inventive molecules in T helper cell lines. TS2 and TS1 are known T helper cell lines, derived from T helper cell clones, which proliferate in the presence of either IL-9 or IL-2 (TS2), and either IL-9 or IL4 (TS1). Specifically, TS1 or TS2 cells were grown in the presence of the listed cytokines for at least 10 days, after which RNA was extracted using known methods. Expression of the molecules was studied via RT-PCR (35 cycles), using the protocols described supra. In TS1 cells both IL-4 and IL-9 induce TIF expression, but IL-2 does not.

Example 18

Expression of TIF mRNA in various mouse organs were studied. Total RNA was prepared from liver, kidney, heart, brain, intestine, spleen, thymus, lung, muscle and bone marrow, using standard guanidium isothiocyanate methodologies and CsCl gradient centrifugation. Forty cycles of RT-PCR were carried out, using the protocols described supra. Strongest expression was found in thymus tissue, while less intense signals were found in brain tissue, and weaker expression in the remaining tissues.

Example 19

The following experiments describe production of TIFα in 293-EBNA cells.

Complementary DNA for TIFα was described supra. It was subcloned into a commercially available expression vector pCEP-4, in operable linkage with a CMV promoter. The resulting plasmids were transfected into 293-EBNA cells, using standard lipofectamine methods. Following transfection, the cells were incubated in a methionine free medium, supplemented with $^{35}$S labeled methionine, for 24 hours. Supernatant was harvested, and run on an acrylamide gel, followed by electrophoresis. The gel was then dried and exposed to autoradiography for 1 day. A control was then run by transfecting cells with the same plasmid, in which the cDNA was cloned in the antisense direction.

A heterogenous band of about 25–30 kilodaltons was found from the cells transfected with TIF in the sense direction. Any discrepancies between the predicted molecular weight, the actual molecular weight in the system, and the heterogeneity, can be attributed to glycosylation.

Example 20

Further experiments were carried out to study production of TIFα in COS cells. Specifically, TIFα cDNA was subcloned into the plasmid pEF-BOS.puro described by Demoulin, et al., supra, in operable linkage with the EF-1α promoter. The plasmid cDNA was transfected into COS cells, using the same lipofectamine method described supra. The cells were incubated in methionine free medium, supplemented with $^{35}$S methionine for 24 hours, after which supernatant was treated as described in example 20, supra. Again, a heterogenous band of 25–30 kilodaltons was observed, as well as an 18 kilodalton band, which probably represents a non-glycosylated form of the molecule.

Example 21

In these experiments, it was discovered that TIF induces STAT activation in mesangial and neuronal cells. It is known that when cytokines activate STAT factors, the factors dimerize, move from cytoplasm to the nucleus, and bind to target sequences in promoters. The details of the experiments follow.

Transfected 293-EBNA cells as described supra were used following incubation in normal medium for 48 hours, as were supernatant from the controls, also described supra. Samples of a mouse kidney mesangial cell line, ("MES13" hereafter), and rat pheochromocytoma cell line ("PC 12" hereafter), were used. Cell samples ($0.5 \times 10^6$), were stimulated for 5–10 minutes in the presence of 1% of supernatant. Nuclear extracts were then prepared, in accordance with Demoulin, et al., Mol. Cell. Biol. 16: 4710 (1996), incorporated by reference. In brief, cells were washed with PBS and then resuspended in 1 ml of ice cold hypotonic buffer for 15 minutes. (Buffer was 10 mM HEPES buffer, pH 7.5, with 10 mM KCl, 1 mM $MgCl_2$, 5% glycerol, 0.5 mM EDTA, 0.1 mM EGTA, 0.5 mM dithiothreitol, and 1 mM Pefabloc, 1 mM $Na_3V_4$, and 5 mM NaF). Cells were then lysed by adding 65 μl of NP-40, followed by vortexing. Nuclei were pelleted, by vortexing for 30 seconds at 14,000 rpm, followed by extraction in buffer supplemented with HEPES (20 mM), glycerol (20%), and NaCl (420 mM). Nuclear debris was removed by centrifuging for 2 minutes. DNA binding activity was determined in accordance with Demoulin et al., supra, using a $^{32}$P labeled double stranded oligonucleotide called "GRR", which contains the STAT binding site of the FcγRI gene promoter, i.e.:
5' ATGTATTTCC CAGAAA-3' (SEQ ID NO: 13) and
5'-CCTTTTCTGG GAAATAC-3' (SEQ ID NO: 14)
corresponding to the upper and lower strands of the binding sites in the GRR probe. Briefly, 5 μl volume of nuclear extracts, were incubated in binding buffer (12 mM HEPES, pH 7.6, 10 mM JO KCl, 0.5 mM EDTA, 2.5% glycerol, 0.1 mg of poly(dI-dC) per ml), for 5 minutes. Radiolabeled GRR probe ($10^5$cpm; approximately 0.5 ng) was added, and incubation was continued for 25 minutes before loading onto a non-denaturing polyacrylamide gel.

It was also noted that the complexes observed in MES13 cells, described supra, were partially overshifted by both anti-STAT5 and anti-STAT3 antibodies, showing that (i) the cells under examination were targets for TIF, and (ii) that STAT3 and STAT5 are major components of the complex activated by TIF.

The foregoing examples describe the invention, one aspect of which are isolated nucleic acid molecules, which encode TIF proteins such as those with the amino acid sequence of the protein encoded by the nucleotide sequence of SEQ ID NO: 7. It will be appreciated by one of ordinary skill that the degeneracy of the genetic code facilitates the preparation of nucleic acid molecules which may not be identical to the nucleotide sequence of SEQ ID NO: 7, but which encode the same protein. Of course, SEQ ID NO: 7 is one preferred embodiment of this invention. Genomic DNA, complementary DNA, and RNA, such as messenger RNA are all to be included therein. A preferred aspect of the invention are isolated nucleic acid molecules whose complements hybridize to SEQ ID NO: 7, or SEQ ID NO: 8, or SEQ ID NO: 9, under stringent conditions. "Stringent conditions", as used herein, refer, for example, to hybridization at 65° C. in buffer (3.5×SSC), 0.02% Ficoll, 0.02% polyvinylpyrrolidone, 0.02% bovine serum albumin, 25 mM $NaH_2PO_4$ (pH 7), 0.1% SDS, 2 mM EDTA, followed by a final wash at 2×SSC, room temperature and then 0.1×SSC/0.2×SDS at temperatures high as, e.g., about 65° C. More stringent conditions, such as 0.1×SSC, can also be used. These nucleic acid molecules encode proteins of about 18 kD, which activates STAT proteins, such as STAT3 and STAT5.

Also a part of the invention are expression vectors which include the nucleic acid molecules of the invention, operably linked to a promoter, so as to facilitate expression of the DNA. It is well within the skill of the artisan to prepare such vectors.

The vectors, as well as the nucleic acid molecules per se, can be used to prepare recombinant cells, be these eukaryotic or prokaryotic, wherein either an expression vector or the nucleic acid molecule itself is incorporated therein. *E. coli* cells, COS cells, CHO cells, etc., are all examples of types of cells which may be used in accordance with this aspect of the invention.

It will be appreciated by the skilled artisan that the proteins encoded by the above recited nucleic acid molecules and are a feature of the invention, may be used to produce antibodies, in accordance with standard protocols. These antibodies can be used, e.g., to determine if the proteins of the invention are present. This is a further feature of the invention, as is now explained. It has been shown, in the examples, that the nucleic acid molecules of the invention were expressed in the presence of the IL-9. Hence, a further feature of the invention is a method to determine if IL-9 is or has been present, wherein one detects either the proteins of the invention, using antibodies for example, or using the nucleic acid molecules of the invention, as probes. Such probes may or may not be labeled, as a matter of choice for the user. Hence, one can determine, for example if, following administration of IL-9, the cytokine is still efficacious, by determining if the nucleic acid molecule of the invention is present. This type of assay can be adapted, for quantitative studies, wherein one determines, for examples, either if a cell is sensitive to IL-9, and if so, how sensitive it is. One can also use the proteins of the invention to phosphorylate of STAT proteins such as STAT3 and STAT5. This in turn results in dimerization of the STAT protein, followed by migration to the nucleus or of anti IL-9 agent to provoke the effect that these STAT proteins have on cells.

One could also use these molecules to test the efficacy of IL-9, when administered to a subject, such as a subject suffering from lymphoma or allergy. The molecules can also be used to mediate the role of IL-9 in these, and other conditions. To elaborate, since IL-9 induces TIFs, the TIFs are useful as IL-9 activity mediators. Thus, a further aspect of the invention is a method to determine activity of endogenous IL-9, such as in situations where excess IL-9 activity is implicated, such as asthmas, allergies, and lymphomas. One can also block or inhibit IL-9 activity by blocking or inhibiting TIF or TIF activity, using, e.g., antisense molecules, antibodies which bind to TIF, or other antagonists of these molecules. "Antibodies" as used herein, refers to any portion of an antibody which binds to TIF, including chimeric and humanized antibodies.

Other features of the invention will be clear to the artisan and need not be discussed further.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. An antibody which specifically binds to a protein encoded by the nucleotide sequence set forth in SEQ ID NO: 7, SEQ ID NO: 8, or SEQ ID NO: 9.

2. The antibody of claim 1, wherein said antibody is a monoclonal antibody.

3. The antibody of claim 1, wherein said antibody is a chimeric antibody or a humanized antibody.

4. The antibody of claim 1, wherein said nucleotide sequence is SEQ ID NO: 7.

5. The antibody of claim 1, wherein said nucleotide sequence is SEQ ID NO: 8.

6. The antibody of claim 1, wherein said nucleotide sequence is SEQ ID NO: 9.

7. The antibody of claim 1, wherein said protein has the amino acid sequence of SEQ ID NO: 15.

8. The antibody of claim 1, wherein said protein has the amino acid sequence of SEQ ID NO: 16.

* * * * *

UNITED STATES PATENT AND TRADEMARK OFFICE
CERTIFICATE OF CORRECTION

PATENT NO. : 6,274,710 B1 Page 1 of 1
DATED : August 14, 2001
INVENTOR(S) : Dumoutier et al.

It is certified that error appears in the above-identified patent and that said Letters Patent is hereby corrected as shown below:

Column 3,
Line 49, change "MM" to -- mM --.

Column 6,
Line 61, change "BW-Phel" to -- BW– Phe --.

Column 7,
Line 27, delete -- 5 --.

Column 9,
Line 55, delete -- JO --.

Signed and Sealed this

Twenty-sixth Day of February, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 6,274,710 B1
DATED : August 14, 2001
INVENTOR(S) : Dumoutier et al.

It is certified that error appears in the above-identified patent and that said Letters Patent is hereby corrected as shown below:

Drawings,
Cancel figure 1.

Column 2,
Lines 59-60, delete in their entirety.

Signed and Sealed this

Third Day of December, 2002

JAMES E. ROGAN
*Director of the United States Patent and Trademark Office*

SEQUENCE LISTING

```
<160> NUMBER OF SEQ ID NOS: 17

<210> SEQ ID NO 1
<211> LENGTH: 24
<212> TYPE: DNA
<213> ORGANISM: Mus musculus

<400> SEQUENCE: 1
agcactctcc agcctctcac cgca                                           24

<210> SEQ ID NO 2
<211> LENGTH: 12
<212> TYPE: DNA
<213> ORGANISM: Mus musculus

<400> SEQUENCE: 2
gatctgcggt ga                                                        12

<210> SEQ ID NO 3
<211> LENGTH: 24
<212> TYPE: DNA
<213> ORGANISM: Mus musculus

<400> SEQUENCE: 3
accgacgtcg actatccatg aaca                                           24

<210> SEQ ID NO 4
<211> LENGTH: 12
<212> TYPE: DNA
<213> ORGANISM: Mus musculus

<400> SEQUENCE: 4
gatctgttca tg                                                        12

<210> SEQ ID NO 5
<211> LENGTH: 24
<212> TYPE: DNA
<213> ORGANISM: Mus musculus

<400> SEQUENCE: 5
aggcaactgt gctatccgag ggaa                                           24

<210> SEQ ID NO 6
<211> LENGTH: 12
<212> TYPE: DNA
<213> ORGANISM: Mus musculus

<400> SEQUENCE: 6
gatcttccct cg                                                        12

<210> SEQ ID NO 7
<211> LENGTH: 1119
```

<212> TYPE: DNA
<213> ORGANISM: Mus musculus

<400> SEQUENCE: 7

| | | | | | |
|---|---|---|---|---|---|
| taaacaggct | ctcctctcac | ttatcaactg | ttgacacttg | tgcgatctct | gatggctgtc | 60 |
| ctgcagaaat | ctatgagttt | ttcccttatg | gggactttgg | ccgccagctg | cctgcttctc | 120 |
| attgccctgt | gggcccagga | ggcaaatgcg | ctgcccgtca | acaccggtg | caagcttgag | 180 |
| gtgtccaact | tccagcagcc | gtacatcgtc | aaccgcacct | ttatgctggc | caaggaggcc | 240 |
| agccttgcag | ataacaacac | agacgtccgg | ctcatcgggg | agaaactgtt | ccgaggagtc | 300 |
| agtgctaaag | atcagtgcta | cctgatgaag | caggtgctca | acttcaccct | ggaagacgtt | 360 |
| ctgctccccc | agtcagacag | gttccagccc | tacatgcagg | aggtggtacc | tttcctgacc | 420 |
| aaactcagca | atcagctcag | ctcctgtcac | atcagcggtg | acgaccagaa | catccagaag | 480 |
| aatgtcagaa | ggctgaagga | gacagtgaaa | agcttggag | agagtggaga | gatcaaggcg | 540 |
| attggggaac | tggacctgct | gtttatgtct | ctgagaaatg | cttgcgtctg | agcgagaaga | 600 |
| agctagaaaa | cgaagaactg | ctccttcctg | ccttctaaaa | agaacaataa | gatccctgaa | 660 |
| tggactttt | tactaaagga | aagtgagaag | ctaacgtcca | tcatcattag | aagatttcac | 720 |
| atgaaacctg | gctcagttga | aaagaaaat | agtgtcaagt | tgtccatgag | accagaggta | 780 |
| gacttgataa | ccacaaagat | tcattgacaa | tattttattg | tcactgatga | tacaacagaa | 840 |
| aaataatgta | ctttaaaaaa | ttgtttgaaa | ggaggttacc | tctcattcct | ttagaaaaaa | 900 |
| agcttatgta | acttcatttc | catatccaat | attttatata | tgtaagttta | tttattataa | 960 |
| gtatacattt | tatttatgtc | agtttattaa | tatggattta | tttatagaaa | cattatctgc | 1020 |
| tattgatatt | tagtataagg | caaataatat | ttatgacaat | aactatggaa | acaagatatc | 1080 |
| ttaggcttta | ataaacacat | ggatatcata | aaaaaaaaa | | | 1119 |

<210> SEQ ID NO 8
<211> LENGTH: 7445
<212> TYPE: DNA
<213> ORGANISM: Mus musculus

<400> SEQUENCE: 8

| | | | | | |
|---|---|---|---|---|---|
| gtctatcacc | tgcttaagat | tcttctaatt | tataaaaaaa | actatttctt | aaaatgaaaa | 60 |
| gcaaccagag | cacgtattta | tagcatggtg | ttctgaccat | gcaggtacag | agtggaatgg | 120 |
| taagaggcgc | tattatcagc | attaaccaac | atgttaatgt | tttcttctgg | caagcaaact | 180 |
| tgaaatctat | gtcttaaaca | atcttcaagc | ctctaatata | gtgctaacga | ctggagtccg | 240 |
| ctgctgtcca | acagagctct | tgagcacgct | ctcctctgtt | tgcaatttta | tgttctttga | 300 |
| tcgactcccc | aacctctcac | cttcggctcc | tgatggccac | cttcaacttt | tctgcattta | 360 |
| tgaactccat | gttttaatct | ttttattaaa | atattcacac | aatcagtgtt | tgtgcaagtc | 420 |
| tgtttcaccc | acatgtatgt | ctgtgcacca | agtgctgcct | ggtgcttgtg | ggcaagga | 480 |
| gcaggagagg | gtgccctggc | accggagtca | cggatggttg | tgagccacca | tgaggatgct | 540 |
| gggagttaga | cccaggtcct | ccagaagtgc | agcaaatgct | cttaaccaca | cgcaggcatt | 600 |
| tctctctcca | gccccaacat | gagtgctttt | agattccacc | tagaatagag | atctgatggc | 660 |
| ttcactcact | gccacctccc | ctttgcatct | ttctgccaag | gaacaccaaa | agcaagaat | 720 |
| ccccacactg | cttcgctcc | tcaagtctgc | acctctcaac | aggtcaagat | tctccagtgt | 780 |
| ccctctaaca | cttttcccag | tgtccctcta | acactttctc | cagtgtccct | ctaacacttt | 840 |

-continued

```
ctccagtgtc cctctaacac ttttgatctc aattagctga ggggagaaag atctcacaca      900
gtgattttca tgacttcgcg ttctagtcta gatgtaggca tttgcgtgtc agtctagggt      960
aggcgtctgc tcccgctgct taggaaagac tttcctagtc tagttgtcag gtgctatctg     1020
ggattcagtg tacatacaat gcaaaaaatc ccagtatttt gtaaattctc ttcttcaact     1080
atccatctat atagtatgtt attgtaggct catttaaaaa taatattttg agacttatgc     1140
ttgcacaagt aaaatgtcag agaattagca aatgtatagt attatttat tttaaaaaaa      1200
tctatgctta aaatgtctat tagattgttc actaccgata tttccaaact taacttgacc     1260
ttggctatga tttcaacctt tgtatttgca tctaccataa cagtctctga accagaacat     1320
tctgtggcaa tgggagctgt gaagaaagcc aacattctta ttaaaaaaaa aaaacagcta     1380
gttatagttt aggattccat atactaaaaa aaatagagat ataattattt taaaaattga     1440
aataatctcc aagttttcat tatggcttat ttcaaagcac agaatatagg cacgggtct      1500
tttatttctg gtcacttcta aagagataag aatctatgaa gttggtggga aaatgagtcc     1560
gtgaccaaaa cgctgactca atagctacgg gagatcaaag gctgctctac tcaatcagaa     1620
tctactacgg caaagccatg gctttctttg aaaaccgtgt ttagaagatt tctgggattt     1680
gtgtgcaaaa gcaccttgtt ggccctcacc gtgacgtttt agggaagact tcccatctct     1740
caaggtggga aggcttggag gtggtgtctt gtggcctcct atggtggtta ggtacttctc     1800
agaagacagg actggaaatt agataatgtc tgatgtcata tcattcacaa taccaaaaaa     1860
accctggtgt cccgatggct ataaaagcag caacttctgc ctctcccatc acaagcagag     1920
acacctaaac aggtaagcac tcagacctct acagacaatc atctgcttgg taccatgcta     1980
cccgacgaac atgctcccct gatgttttg ccttttgctc tctcactaac aggctctcct      2040
ctcacttatc aactgttgac acttgtgcga tctctgatgg ctgtcctgca gaaatctatg     2100
agttttccc ttatggggac tttggccgcc agctgcctgc ttctcattgc cctgtgggcc      2160
caggaggcaa atgcgctgcc cgtcaacacc cggtgcaagc ttgaggtgtc caacttccag     2220
cagccgtaca tcgtcaaccg cacctttatg ctggccaagg aggtacagct gcatctcttt     2280
ctctccatac cgccttgcca ttttctctga agcacttgca aactctttag gggcgcttta     2340
tctccgcagg tctcactacc tatgtttct gtctcttta gactcttta aggactgggt        2400
cttttttctat ttctatttca aggtctcagg accatttcct atcttggcct tcaggacaca    2460
tatactgaat tttatctaca gaggcgcatt tagaaagcca cccacgactg caatactttc     2520
catttctctg tgctctcttc tgaactcata ctctcttggc tactcctgag acccactgcg     2580
gacatacatc tctacttaca ggcttttctt ccatctcctt gtcacccagg cacttagggt     2640
tttctctctt tcaggccagc cttgcagata caacacaga cgtccggctc atcggggaga      2700
aactgttccg aggagtcagt gtaagtcctc actgtgatga gcagggctag ctgcgggagc     2760
tggtggaccc tctgggatag tctgacgtat gaccectgct gcttcttgtc tacctgcagg     2820
ctaaagatca gtgctacctg atgaagcagg tgctcaactt caccctggaa gacgttctgc     2880
tccccccagtc agacaggttc cagccctaca tgcaggaggt ggtacctttc ctgaccaaac    2940
tcagcaatca gctcagctcc tgtgtaagtc tgactctggc tacctatgct cctctctctt     3000
cctcttctat tccagtaaga acccgaggtc ctgccctctc tctcttcaca agagtgagga    3060
gggcctcagc accaccacca tcataggcca cttgaaatag gtcacaaagg ctttggcttc    3120
aattgagtaa tactttgagt ttgtatgagt gaagcttat ttgttttatc catggaaaga     3180
aatcaactca aattctgtag gatgagaaag atgttgggaa cgaaaaaagg cctagataga    3240
```

-continued

```
gaaacagatc tgctgagtat agtacttatg gggggagcag ggggcgatat ccactgagta      3300
caagtacttg tggggagaga aatccactga gtacaagtac ttgttggcat ggagatccac      3360
tgagtacaag tacttgtggg gggagggaat ggcacagagc aaaagttgaa gggaaggaag      3420
atggagaggc ctcatggttg ggggtgtgaa aggtcactcc ttttccatgt gatggagagt      3480
taagaaaaac cagtgtgtga gtttgatgtc ttcagacacc cccaactatg aaacatatcc      3540
acgaggagcg ggcagactgt gggagacctg gcatttaggg aaggcgcggc ttttcacacg      3600
agaaacttta tgctcatctc ttgtgctaca ctcccacctt tgatgaggtt cagctcaggt      3660
ttcgtttcta ccgttcttgc tactggtgga aacttcagta ggattcccca aagacgagga      3720
cagctcttct gtaagggagg gacctggatt tcagtgtcct agagaacgaa atagctcaga      3780
gaatctaggt caacgtgaaa tctaggtcac agcgggcaaa aatgactgaa cgcctctatt      3840
ccaggtgaac ggtcacgtgc ctcagatata ctgaggtatt gggctcccac cggataagat      3900
tctgttagtg agtctgcttt tattttgcag cacatcagcg gtgacgacca gaacatccag      3960
aagaatgtca gaaggctgaa ggagacagtg aaaaaggtac tattggcaag ccacaatact      4020
aagccattca gtaggagacg tgggggattc ttttctctgct tcccagtccc ttctactttg      4080
taacatttta tttgacttgt ctactatctg gtccattact cgcttagctg cacctgtatc      4140
tagctgggtc tatagatctt tcaatctgtg tctaaatttg taagtcacaa ttctggagct      4200
agcagaaagc ttagctcagc cagtctcatg agcacttgct cggaggatgg cttgtgacag      4260
agtcaatgct agaagacagc atccctgatt cccagctctg cacttgccta gtggccatgt      4320
gtaattactt tggcttgatt aagtatttgg gaaagccagt tcccacggac ctacataatc      4380
tgaagaacca tgcattgaaa actagaaagc tgggcacaaa cttactagag atgattttttg      4440 agctcattaa acggatgctc tgaaatgtgg caaaatcaac ccagaataac aacaaaagag      4500
ctggatttgc aaataggaca agtatttaga atcactggta ttaatagcta tcatcttaat      4560
taaaatatag ggcctatata tatatttaag attaaacaca agagtggata gcctcccaat      4620
ttacttggcc tggtttcaaa agagtaaaaa tatcagtcat ggattaatta tagtgtcatg      4680
aaagtatgag atggaaaccc tttccttact ttttaccttc atttcttagt tttttttttc      4740
ttcacaccct gatcaagcca ctagtaagca cctatctgct gtgagctatt atatgacttt      4800
acagcaaaca acattgctgt gtggcctctt tggggaaggg aacaggatag caggaggctc      4860
aggctagcaa gtctgacttg ccctaaagcc agaggcatgg ttgatagcag agaaagtgag      4920
gctcttcgca gtgggtgtg cttaagtaat cagaaacagg aaggctccgg ttgatggaat      4980
tatcagtaag atatctaccc ttatctcctt ctatcgaacc taaatcgtct cttttttcttg      5040 tgtgtaggct gataaacaca cttgttttct tttgagtgtt catggctttg tagattttta      5100
gtgctctgcc agttcttgtt agagggtttg ttaccttgac acctgggctt ggatgttagc      5160
atgccaaagg cacacacttc tgaatgcctg tgtaaaaggt tattattcat ttactttgtc      5220
tttgaaaagg tgaagcgtgt gtgagaaaga actcacagga gatgtgttct ctgtaggaaa      5280 acttttttttt tccccttaaa tgcctataat ccactttcag tcaactttga cttttatacc      5340
atgctgtcac atgaaaagt gtttaggccc gctctcatgg ctctgggaaa agcaccaata      5400
ggggaaggaa tgttatgctg agaaatctga ccggcaggga aactggtcag agctcccccg      5460
aagaccacca caggtgttaa gtaggaacag tccagggtgg gctcatgtaa tagaatggaa      5520
cagagcgagg gaagataagc tacaaagttt catagggtcc ggagtcttaa agatacaaaa      5580
```

```
tagctgcttg ggcttcataa caaaggaagt ctgggaaggc agcaagtgag agggaaatgg      5640
aaagggaaaa aacagaatgt agaggacttg aacagctaca aatcctctac cagacgattt      5700
ttcttggaac aatctagaag gtagtggatt aggtgattgc aggggacttt gctttgccat      5760
ttgaatctgg gttttttgtct ctccattgag gttgaaagcg tcacccttttt taccctcgaa    5820 tggaggagga aagaagggt gttatgactc ctacctggag ttttactagt ttacgcaatg       5880
gaacagacac tcgggacctc ctcttgacaa aaaaaatgga aacctgttgt ttgtcttgtt      5940 tgttctttttg ttaagaaagc acaggcaaag cccgaccaca tggttgaat gtgggtctttt     6000 gagtcaaggc tttttgagttg agcactcatc aatagttgat catggtcagg tggagggcta    6060
cctgtcaggc cgagccctgc tggcttcgca cttaacatct ccaggtctca gtatcacttc      6120
ctgctactta gcacagttag gagttgagca aacctttttt tccaacccccc actaaaattt    6180 aattgacaaa agactgtgta atttgtggga tacagtgtga taattgatct atgtgtgcat      6240
tgtgcaaggt tcaataagat agattaatag gcccatcaac agctttatgg gtgtgaaatg     6300
caagtaatat aggtagatgc ctgtggtgtc cttaggtcag aaaggcatga ttttaaggtc     6360
ttgggcaaat catatattac tcatgctaaa aatacattat gttgattatt aatcttttag     6420
agaaggctga tacttggttt tggtgctcag caagcaaatg tcaccagctc tttctaactg     6480
gtaccacttt agaaaatgct acctgtgctc aaattggttt gtattcttat tttcatagct     6540
tggagagagt ggagagatca aggcgattgg ggaactggac ctgctgttta tgtctctgag    6600
aaatgcttgc gtctgagcga gaagaagcta gaaaacgaag aactgctcct tcctgccttc     6660
taaaaagaac aataagatcc ctgaatggac ttttttacta aaggaaagtg agaagctaac     6720
gtccatcatc attagaagat ttcacatgaa acctggctca gttgaaaaag aaaatagtgt     6780
caagttgtcc atgagaccag aggtagactt gataaccaca aagattcatt gacaatattt    6840
tattgtcact gatgatacaa cagaaaaata atgtacttta aaaaattgtt tgaaaggagg    6900
ttacctctca ttcctttaga aaaaagctt atgtaacttc atttccatat ccaatatttt      6960
atatatgtaa gttatttat tataagtata cattttattt atgtcagttt attaatatgg      7020
atttatttat agaaacatta tctgctattg atatttagta taaggcaaat aatatttatg    7080
acataactca tggaaacaag atatcttagg ctttaataaa cacatggata tcataaatct     7140
tctgtcttgt aattttttctc cctttaatat caacaatacc atcatcatca tcattaccca    7200
atcattctca tgatttcatg cttgacccat attatactgt taaagttggt tcctggaggc     7260
ctgtggtttt gtgtgtgttg tgtgtgtgtg tggggttatg catgtgaaag ccagagatgg    7320
atattaggtg ttcttctcta tcagtctttg ccttattatt tgagacaggg tctgtcactg    7380
aacctgtagc taggctggcc aacaagctct attaattttt tttaagatta attaattatg     7440
tgtat                                                                 7445
```

<210> SEQ ID NO 9
<211> LENGTH: 1111
<212> TYPE: DNA
<213> ORGANISM: Mus musculus

<400> SEQUENCE: 9

```
aacaggctct cctctcagtt atcaactttt gacacttgtg cgatcggtga tggctgtcct       60
gcagaaatct atgagttttt cccttatggg gactttggcc gccagctgcc tgcttctcat     120
tgccctgtgg gcccaggagg caaatgcgct gcccatcaac acccggtgca agcttgaggt     180
gtccaacttc cagcagccgt acatcgtcaa ccgcaccttt atgctggcca aggaggccag    240
```

-continued

```
ccttgcagat aacaacacag acgtccggct catcggggag aaactgttcc gaggagtcag    300
tgctaaggat cagtgctacc tgatgaagca ggtgctcaac ttcaccctgg aagacattct    360
gctcccccag tcagacaggt tccggcccta catgcaggag gtggtgcctt tcctgaccaa    420
actcagcaat cagctcagct cctgtcacat cagtggtgac gaccagaaca tccagaagaa    480
tgtcagaagg ctgaaggaga cagtgaaaaa gcttggagag agcggagaga tcaaagcgat    540
cggggaactg gacctgctgt ttatgtctct gagaaatgct tgcgtctgag cgagaagaag    600
ctagaaaacg aagaactgct ccttcctgcc ttctaaaaag aacaataaga tccctgaatg    660
gactttttta ctaaaggaaa gtgagaagct aacgtccacc atcattagaa gatttcacat    720
gaaacctggc tcagttgaaa gagaaaatag tgtcaagttg tccatgagac cagaggtaga    780
cttgataacc acaaagattc attgacaata ttttattgtc attgataatg caacagaaaa    840
agtatgtact ttaaaaaatt gtttgaaagg aggttacctc tcattcctct agaagaaaag    900
cctatgtaac ttcatttcca taaccaatac tttatatatg taagtttatt tattataagt    960
atacatttta tttatgtcag tttattaata tggatttatt tatagaaaaa ttatctgatg   1020
ttgatatttg agtataaagc aaataatatt tatgataata actatagaaa caagatatct   1080
taggctttaa taaacacatg aatatcataa a                                  1111
```

<210> SEQ ID NO 10
<211> LENGTH: 21
<212> TYPE: DNA
<213> ORGANISM: Mus musculus

<400> SEQUENCE: 10
ctgcctgctt ctcattgccc t                                              21

<210> SEQ ID NO 11
<211> LENGTH: 21
<212> TYPE: DNA
<213> ORGANISM: Mus musculus

<400> SEQUENCE: 11
caagtctacc tctggtctca t                                              21

<210> SEQ ID NO 12
<211> LENGTH: 20
<212> TYPE: DNA
<213> ORGANISM: Mus musculus

<400> SEQUENCE: 12
gacgcaagca tttctcagag                                                20

<210> SEQ ID NO 13
<211> LENGTH: 16
<212> TYPE: DNA
<213> ORGANISM: Homo sapiens

<400> SEQUENCE: 13
atgtatttcc cagaaa                                                    16

<210> SEQ ID NO 14
<211> LENGTH: 17
<212> TYPE: DNA
<213> ORGANISM: Homo sapiens

<400> SEQUENCE: 14

```
cctttctgg gaaatac                                                        17
```

<210> SEQ ID NO 15
<211> LENGTH: 179
<212> TYPE: PRT
<213> ORGANISM: Mus musculus

<400> SEQUENCE: 15

Met Ala Val Leu Gln Lys Ser Met Ser Phe Ser Leu Met Gly Thr Leu
1               5                   10                  15

Ala Ala Ser Cys Leu Leu Leu Ile Ala Leu Trp Ala Gln Glu Ala Asn
            20                  25                  30

Ala Leu Pro Val Asn Thr Arg Cys Lys Leu Glu Val Ser Asn Phe Gln
        35                  40                  45

Gln Pro Tyr Ile Val Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

Arg Gly Val Ser Ala Lys Asp Gln Cys Tyr Leu Met Lys Gln Val Leu
                85                  90                  95

Asn Phe Thr Leu Glu Asp Val Leu Leu Pro Gln Ser Asp Arg Phe Gln
            100                 105                 110

Pro Tyr Met Gln Glu Val Val Pro Phe Leu Thr Lys Leu Ser Asn Gln
        115                 120                 125

Leu Ser Ser Cys His Ile Ser Gly Asp Asp Gln Asn Ile Gln Lys Asn
    130                 135                 140

Val Arg Arg Leu Lys Glu Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Val

<210> SEQ ID NO 16
<211> LENGTH: 179
<212> TYPE: PRT
<213> ORGANISM: Mus musculus

<400> SEQUENCE: 16

Met Ala Val Leu Gln Lys Ser Met Ser Phe Ser Leu Met Gly Thr Leu
1               5                   10                  15

Ala Ala Ser Cys Leu Leu Leu Ile Ala Leu Trp Ala Gln Glu Ala Asn
            20                  25                  30

Ala Leu Pro Ile Asn Thr Arg Cys Lys Leu Glu Val Ser Asn Phe Gln
        35                  40                  45

Gln Pro Tyr Ile Val Asn Arg Thr Phe Met Leu Ala Lys Glu Ala Ser
    50                  55                  60

Leu Ala Asp Asn Asn Thr Asp Val Arg Leu Ile Gly Glu Lys Leu Phe
65                  70                  75                  80

Arg Gly Val Ser Ala Lys Asp Gln Cys Tyr Leu Met Lys Gln Val Leu
                85                  90                  95

Asn Phe Thr Leu Glu Asp Ile Leu Leu Pro Gln Ser Asp Arg Phe Arg
            100                 105                 110

Pro Tyr Met Gln Glu Val Val Pro Phe Leu Thr Lys Leu Ser Asn Gln
        115                 120                 125

Leu Ser Ser Cys His Ile Ser Gly Asp Asp Gln Asn Ile Gln Lys Asn
    130                 135                 140

```
Val Arg Arg Leu Lys Glu Thr Val Lys Lys Leu Gly Glu Ser Gly Glu
145                 150                 155                 160

Ile Lys Ala Ile Gly Glu Leu Asp Leu Leu Phe Met Ser Leu Arg Asn
                165                 170                 175

Ala Cys Val

<210> SEQ ID NO 17
<211> LENGTH: 5935
<212> TYPE: DNA
<213> ORGANISM: Mus musculus

<400> SEQUENCE: 17
gaattcaagt ccacatgcaa tcaatccgaa tactttgtaa attctcttct tcaaatatcc      60
atctatatag tataagttat tgtaggatca tttaaaaata atgttttgag acttatgttt     120
gcacaagtaa aatgtcagag agaattagca aatgtatagt attattttat tttaaaaaat     180
ctatgcttaa aatgtctatt agattgttca ctactgacat ttccaaactt aacttgacct     240
tggctatgat ttcaaccttt gtatttgcat ctaccataac tgtgtgctca cttaccatgc     300
tatccgacga gcatgttccc ctgatgtttt tgccttttgc tctctcgcta acaggctctc     360
ctctcagtta tcaactttg acacttgtgc gatcggtgat ggctgtcctg cagaaatcta     420
tgagtttttc ccttatgggg actttggccg ccagctgcct gcttctcatt gccctgtggg     480
cccaggaggc aaatgcgctg cccatcaaca cccggtgcaa gcttgaggtg tccaacttcc     540
agcagccgta catcgtcaac cgcaccttta tgctggccaa ggaggtacag ctgcatctct     600
ttctctccat accgccttgc catttctctg aagcacttgc aaactcttta ggggcgcttt     660
atctccgcag gtctcactac ctatgttttc tgtctcttta gagactcttt aaggactgga     720 tcttttttcta tttctatttc aaggtctcag gaccatttcc tatcttggcc ttcaggacac     780
atatactgaa ttttatctac agaggcgcgt ttagaaagcc acccacgact gcaatacttt     840
ccatcctgtt gtgctctctt ctgaactcat actctcttgg ctactcctga acccactgc     900 ggacatacat ctctacttac aggcttttct tccatctcct tgtcacccag gcacttaggg     960
ttttctctct ttcaggccag ccttgcagat aacaacacag acgtccggct catcggggag    1020
aaactgttcc gaggagtcag tgtaagtcct cactgtgatg agcagggcta gctgcggag    1080 ctggtggacc ctctgggata gtctgacgta tgacccctgc tgcttcttgt ctacctgcag    1140
gctaaggatc agtgctacct gatgaagcag gtgctcaact tcaccctgga agacattctg    1200
ctcccccagt cagacaggtt ccggccctac atgcaggagg tggtgccttt cctgaccaaa    1260
ctcagcaatc agctcagctc ctgtgtaagt ctggctctgg ctacctatgc tcctctctct    1320
tcctcttcta ttccagtaag aacccgaggt cctgccctct ctctcttcac aagagtgagg    1380
agggcctcag caccaccacc atcataggcc acttgaaata ggtcacaaag gctttggctt    1440
caattgagta atactttgag tttgtattag ttaagcttta tttgttttat ccatggaaag    1500
aaatcaactc aaattctgta ggatgagaaa gatgttggga acgaaaaaag gcctagatag    1560
agaaacagat ctgctgagta cagtacttat ggggggggggg ggcaggggc gatatccact     1620 gagtccaagt acttgttggg agagaaatcc actgagtaca agtacttgtg ggggaaggaa    1680
tggcacagag caaagttga agggaaagag gaagatggag aggcctcaat gttggggtg     1740 tgaaaggtca ctcctttttc catgtgatgg agagttaaga aaaatcagtg tgtgagtttg    1800
atgtcttcag acaccccaac tatggcagac tgtgggagac ctggcattta gggaaggcgc    1860
```

-continued

```
ggcttttcac acgagaaact ttatgctcat ctcttgtgct acactcccac ctttgatgag    1920
gttaagctca ggtttcgttt ctaccgttct tgctactggt ggaaacttca gtaggattcc    1980
ccaaagacga ggacagctct tctgtaaggg agggacctgg atttcagtgt cctagagaac    2040
gaaatagctc agagaatcta ggtcaacgtg aaatctaggt cacagcgggc aaaaatgact    2100
gaacgcctct attccaggtg aacggtcacg tgcctcagat atactgaggt attgggctcc    2160
caccggataa gattctgtta gtgagtctgc ttttattttg cagcacatca gtggtgacga    2220
ccagaacatc cagaagaatg tcagaaggct gaaggagaca gtgaaaaagg tactattggc    2280
aagccacaat actaagccat tcagtaggag acgtggggat ttctttctct gcttcccagt    2340
ctcttctact ttgtaacatt ttctttgact tgtctactgt ctggtccatt actcacttag    2400
ctgcacctgc atctagctgg gtctatagat ctttcaatct gtgtctaaat ttgtaagtca    2460
caattctgga gctagcagaa agcttagctc agccagtctc atgagcactt gctcggagga    2520
tggcttgtga cagagtcaat gctagaagac agcatccctg attcccagct ctgcacttgc    2580
ctagtggcca cgtgtaatta ctttagcctg attaagtatt tgggaaagcc aattcccacc    2640
gacctacata atccgaagaa gcatgcattg aaaactagaa agctgggcac aaacttacta    2700
gagatgattt tgagctcat taaactgatg ctctgaaatg tgatcaaatc aacccagaat    2760
aacaacaaaa gagctggatt tgcaaatagg acaagtattt agaatcactg gtattaacag    2820
ctgtcatctt aattaaaata tagtgtctat ttagctgcct atttaagatt aaacacaaga    2880
gtggataact tcccaattta ctgggcctgg tttcaataga gtaaaaatat cagtcataga    2940
ttaattatag tgtcatgaaa gtatgagttg gaaacccttt ccttacttt taccttcatt    3000
tcttagttat tattttttt tcttcacacc ctgatcaagc cactagtaag cacctatctg    3060
ctgcgagcta ttatatgact ttacagcaaa caacattgct gtgtggcctc tttggggaag    3120
ggaacaggat agcaggaggc tcaggctagc aagtctggac tcaacctaaa gccagaggca    3180
tggttgatag cagagaaagt gaggctcttc acaagtgggt gtgcttaagt aatcagaaac    3240
aggaaggctc tggttgatgg aattatcagt aagatatcta cccttatctc cttcttctat    3300
agaagctaaa ccgtctctcc ttcttgtgtg taggctgata acacgcttg ttttcttttg    3360
agtgttcatg gctttgcaga ttttcagtgc tctgccagtt cttgttagag ggtttgttac    3420
cttgacacct gggcttggat gttagcatgc caaaggcaca cacttctgaa tgcctgtgta    3480
aaaggttatt attcatttac tttgtctttg gaaaggtgaa gtgtgtgtga gaaagaactc    3540
acaggagatg tattctctgt aggaaaactt ttttttcccc ttaaaagcct ataatccact    3600
ttcagtcaac tttgactttt ataccatgct gtcacatgaa agagtgttta ggcccgctct    3660
cgtggctctg ggaaaagcac caatagggga agaaatgtta tgccgagaaa tctgactggc    3720
agggaaactg ggtcagagct ccccaaagac cactacaggt gttaagtagg aacagtcgag    3780
ggtgggttca tataatagaa tggaacagag ggagggaaga taagctacaa agtttcatag    3840
ggtcctaagt ctttaagata caaaatagct ggttgggctt cataacaaag gaagtctggg    3900
aaggcagcaa gcattgagag ggagatggaa agggaaaaaa caatgtagag gatttgaaaa    3960
gctacaaatc ctccacgaga ggattttcct tggaggaatc tagaacaagg gtggtggatt    4020
aggtggatcg cagaaggact tgctttgcca tttgaatctg ggttttttgtc tctccattga    4080
ggttgagagc gtcacccttt tttaccctgg ataggaggag gaaagaaggg gtgttttgac    4140
tcctacctgg agttttacta gttacgcaa tggaacagac actcgggacc tcctcttgac    4200
aagaaaaaaa aaaaaaaaag gaaacctgtt gtttctcttg tttgttcttt tgttaagaaa    4260
```

```
gcacaggcag ctgggcatgg tggcccatgc ctttaatccc agcatttggg aggcagaggc    4320
aggtgacttt ctaaattcaa ggccagcctg gtctacaaag tgagttccag gacagccagg    4380
gctatacaga gaaaccctgt ctcgggaaaa aaaaaaaaga agaaaagaaa agaaaagaag    4440
agaagaggag aggagaggag aggagaggag aggagaggag aggagaggag aggagaggag    4500
aggagaggag aagagaagag aagagaagag aagagaagag aagagaagag aagagaagag    4560
aagagaagag aagagaagag aagagaagag aagagaagag aagagaaaag aaaagagaaa    4620
agaaaagaaa aaagcaagca agcaagcact ggcaaagcat gcccacatgg gacgtatgtg    4680
ggtctttgag acaaggcttt tgaattgagc gctcatcaat agttgatcat ggtcaggtgg    4740
agggctacct gtcaggccga gccctgctgg cttagcactt aacatctcca ggtctcagta    4800
tcacttcctg ctgcttagca cagttaggag ttgagcaaac ctttttttcc aacccccact    4860
aaaatttaat ttacaaaagg cagtgtaatt tgtgggatac agtgtgataa ttgatctatg    4920
tgtgcattgt gcaaggttca ataaggtaga tcaataggcc catcaacagc tttatgggtg    4980
tgaaatgcaa gtaatatagg tagatgcctg tgtgtcctta ggtcagaaag gcatgatttt    5040
aaggtcttgg gcaaatcata ttatactcat gttaaaaatg cattatgttg attatcaatc    5100
ttttagagaa ggctgatact tggttttggt gctcagcaag caaatgtcac cagctctttc    5160
taactagtac cactttagaa aatgctaccc gtgctcaaat tggtttgtat tcttattttc    5220
atagcttgga gagagcggag agatcaaagc gatcggggaa ctggacctgc tgtttatgtc    5280
tctgagaaat gcttgcgtct gagcgagaag aagctagaaa acgaagaact gctccttcct    5340
gccttctaaa aagaacaata agatccctga atggactttt ttactaaagg aaagtgagaa    5400
gctaacgtcc accatcatta gaagatttca catgaaacct ggctcagttg aaagagaaaa    5460
tagtgtcaag ttgtccatga gaccagaggt agacttgata accacaaaga ttcattgaca    5520
atattttatt gtcattgata atgcaacaga aaaagtatgt actttaaaaa attgtttgaa    5580
aggaggttac ctctcattcc tctagaagaa aagcctatgt aacttcattt ccataaccaa    5640
tactttatat atgtaagttt atttattata agtatacatt ttatttatgt cagtttatta    5700
atatggatttt atttatagaa aaattatctg atgttgatat ttgagtataa agcaaataat    5760
atttatgata ataactatag aaacaagata tcttaggctt taataaacac atgaatatca    5820
taaatcttct gtcttgtaat ttttctccct ttaatatcaa caataccatc atcgtcatca    5880
ttacccaatc attctcatga cttcatgctt gactcatatt atctggtaaa gtttg         5935
```